United States Patent [19]

Müller et al.

[11] 4,276,423
[45] Jun. 30, 1981

[54] PROCESS FOR PREPARING SILICON-CONTAINING ACETAMIDE DERIVATIVES

[75] Inventors: Horst Müller, Emmerting; Volker Frey, Burghausen, both of Fed. Rep. of Germany

[73] Assignee: Wacker-Chemie GmbH, Munich, Fed. Rep. of Germany

[21] Appl. No.: 158,091

[22] Filed: Jun. 10, 1980

[30] Foreign Application Priority Data

Jun. 11, 1979 [DE] Fed. Rep. of Germany ....... 2923604

[51] Int. Cl.$^3$ .............................................. C07F 7/10
[52] U.S. Cl. ................................................... 556/411
[58] Field of Search ......................................... 556/411

[56] References Cited

U.S. PATENT DOCUMENTS

| | | |
|---|---|---|
| 2,876,209 | 3/1959 | deBenneville et al. .......... 556/411 X |
| 2,876,234 | 3/1959 | Kurwitz et al. .................. 556/411 X |
| 3,701,795 | 10/1972 | Kolub et al. .......................... 556/411 |
| 3,966,531 | 6/1976 | Bargain ............................. 556/411 X |

*Primary Examiner*—Paul F. Shaver

[57] ABSTRACT

A process for preparing silicon-containing acetamide derivatives which comprises reacting acetamide or substituted derivatives thereof with N-trimethylsilyl imidazole while continuously removing the silicon-containing acetamide derivatives as they are formed by distillation.

6 Claims, No Drawings

PROCESS FOR PREPARING SILICON-CONTAINING ACETAMIDE DERIVATIVES

The present invention relates to a process for preparing acetamide derivatives and more particularly to a process for preparing silicon-containing acetamide derivatives.

BACKGROUND OF INVENTION

Several processes for preparing silicon-containing acetamide derivatives are described in U.S. Pat. No. 3,397,220 to Klebe. One method for preparing the silicon-containing acetamide derivatives is to react one mole of trimethylchlorosilane with one mole of acetamide or N-methyl-acetamide in the presence of a hydrohalide acceptor such as trimethylamine or pyridine. Also, a process for preparing bis-(trimethylsilyl)-acetamide is described in which two moles of trimethylchlorosilane are reacted with one mole of acetamide in the presence of a hydrohalide acceptor.

In contrast to the processes described in the above patent for preparing silicon-containing acetamide derivatives, the process of this invention has certain advantages. For example, it does not require the use of toxic amines. Moreover, the process of this invention is more efficient since it does not require separating the silicon-containing acetamide derivatives from the amine hydrochloride. Furthermore, higher yields of the desired silicon-containing acetamide derivatives are obtained from the process of this invention.

Therefore, it is an object of this invention to provide a process for preparing acetamide derivatives. Another object of this invention is to provide a process for preparing silicon-containing acetamide derivatives. A further object of this invention is to provide a process for preparing high yields of silicon-containing acetamide derivatives in the absence of hydrohalide acceptors.

SUMMARY OF INVENTION

The foregoing objects and others which will become apparent from the following description are accomplished in accordance with this invention, generally speaking, by reacting acetamide or substituted derivatives thereof with N-trimethylsilyl imidazole at a temperature of from about 40° C. up to about 180° C., while continuously removing the silicon-containing acetamide derivatives as they are formed by distillation.

DETAILED DESCRIPTION OF INVENTION

The silicon-containing acetamide derivatives, which are obtained from the process of this invention by reacting acetamide and substituted derivatives thereof with N-trimethylsilyl imidazole may be represented by the formulas

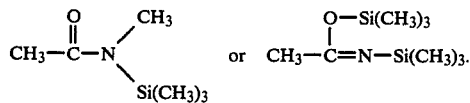

Examples of substituted derivatives of acetamide are N-methylacetamide and N-trimethylsilyl acetamide.

Acetamide and substituted acetamides such as N-trimethylsilyl acetamide as well as N-trimethylsilyl imidazole are well known in the art. The preparation of N-trimethylsilyl acetamide is described in U.S. Pat. No. 3,839,387 to TaSen Chou et al. The N-trimethylsilyl imidazole is described in "Angewandte Chemie", Vol. 77, 1965, page 414.

In the process of this invention, N-trimethylsilyl imidazole is preferably used in amounts of at least 1 mole for each mole of N-trimethylsilyl acetamide, or N-methylacetamide, or in an amount of at least 2 moles per mole of acetamide. To further accelerate the reaction, the mixture containing the reactants is preferably heated to a temperature of from 40° to 180° C.

The silicon-containing acetamide derivatives are prepared by mixing the N-trimethylsilyl imidazole with the N-methylacetamide, or the N-trimethylsilyl acetamide and/or the acetamide. The silicon-containing acetamide derivatives may also be prepared by reacting acetamide or N-methylacetamide with at least one mole of imidazole and at least 1 mole of hexamethyldisilazane in the presence of a silylization catalyst such as ammonium chloride, if desired, at a temperature of from 40° to 125° C. When the formation of ammonia has ceased, the excess hexamethyldisilazane is removed by distillation, and after additional heating, the desired silicon-containing acetamide derivative is distilled off.

It is preferred that the reaction mixture containing the acetamide and/or N-trimethylsilyl acetamide, or the N-methylacetamide and the N-trimethylsilyl imidazole be agitated in order to provide a homogeneous reaction mixture and prevent localized concentration and heating.

If desired, the reaction may take place in a solvent which is inert to the reactants and which has a higher boiling point than the reactants and the desired silicon-containing acetamide derivative. Examples of suitable solvents are trimethylsiloxy endblocked dimethylpolysiloxanes and decahydronaphthalene.

The equipment used for the distillation of the desired derivative of the acetamide as it is formed, which may be either bis-(trimethylsilyl)-acetamide or N-methyl-N-trimethylsilyl acetamide, may be a column which is equipped with fractionation devices such as packing, sieve trays or bubble plates.

It is preferred that the process of this invention be carried out under anhydrous conditions and under a pressure which does not exceed atmospheric pressure, i.e., about 1 bar, and more preferably at pressures of from 10 to 100 mbar.

The invented process may be conducted batch-wise, semi-continuously or as a continuous process.

If desired, the silicon-containing acetamide derivative obtained from the process of this invention may be further purified, for example by distillation.

The imidazole obtained from the process of this invention by removing the bis-(trimethylsilyl)-acetamide, or the N-methyl-N-trimethylsilyl acetamide from the reactive mixture by distillation, can again be converted into N-trimethylsilyl imidazole, for example by means of hexamethyldisilazane. The N-trimethylsilyl imidazole thus obtained can then be reacted with N-methylacetamide or with N-trimethylsilyl acetamide and/or acetamide.

EXAMPLE 1

About 262 g (2 mole) of N-trimethylsilyl acetamide and 420 g (3 mole) of N-trimethylsilyl imidazole are added to a 1-liter flask, provided with a packed column 140 cm in length and having an inside diameter of 3 cm. The contents of the flask are heated to boiling at a pressure of 65 mbar, so that the temperature of the reactants is between 120° and 170° C.

The distillate passed from the top of the column at a maximum temperature of 80° C. After about 10 hours, the reaction is complete.

The distillate consists of 406 g of a liquid consisting of approximately 90 percent by weight of bis-(trimethylsilyl)-acetamide. The remainder of the distillate consists of N-trimethylsilyl imidazole and N-trimethylsilyl acetamide, in addition to traces of hexamethyldisiloxane. After additional fractional distillation, this distillate yields 385 g of bis-(trimethylsilyl)-acetamide having a purity of 95 percent by weight (boiling point at 40 mbar: 70° C.; $d^{25}=0.83$ g/cm$^3$; $n_D^{25}=1.416$), which corresponds to a yield of about 90 percent by weight of theory.

The distillation residue consists of imidazole and excess N-trimethylsilyl imidazole.

EXAMPLE 2

The process described in Example 1 is repeated, except that 2 mole of acetamide and 5 mole of N-trimethylsilyl imidazole is used. Essentially the same results are obtained.

EXAMPLE 3

About 146 g (2 mole) of N-methylacetamide and 420 g (3 mole) of N-trimethylsilyl imidazole are placed in a 1-liter flask provided with a packed column 140 cm in length and an inside diameter of 3 cm. The contents of the flask are heated to boiling at 13 mbar, so that the temperature of the reactants is between 120° and 170° C.

The distillate passes from the top of the column at a maximum temperature of 50° C. The reaction is complete after approximately 8 hours.

The distillate consists of 310 g of a liquid consisting of about 90 percent by weight of N-methyl-N-trimethylsilyl acetamide. The remainder is N-trimethylsilyl imidazole and unreacted N-methylacetamide, and traces of hexamethyldisiloxane. After additional fractional distillation, the distillate yields 289 g of N-methyl-N-trimethylsilyl acetamide with a purity of about 95 percent (b.p. 50° C. at 15 mbar; $d^{25}=0.9$ g/cm$^3$; $n_D^{25}=1.438$), which corresponds to a yield of about 95 percent of theory.

As in Example 1, the distillation residue consists of imidazole and excess N-trimethylsilyl imidazole.

What is claimed is:

1. A process for the preparation of silicon-containing acetamide derivatives, which comprises reacting acetamide or substituted derivatives thereof with N-trimethylsilyl imidazole while continuously removing the silicon-containing acetamide derivatives as they are formed by distillation.

2. The process of claim 1, wherein the silicon-containing acetamide derivatives may be represented by the general formula

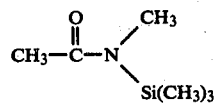

3. The process of claim 1, wherein the silicon containing acetamide derivatives may be represented by the general formula

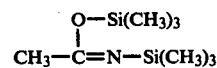

4. The process of claim 1, wherein the substituted derivative of acetamide is selected from the group consisting of N-methyl acetamide and N-trimethylsilyl acetamide.

5. The process of claim 1, wherein the reaction is conducted at a temperature of from 40° to 180° C.

6. The process of claim 1, wherein at least one mole of acetamide is reacted with 2 moles of N-trimethylsilyl imidazole.

* * * * *